United States Patent [19]
Hoffmann et al.

[11] Patent Number: 5,304,290
[45] Date of Patent: Apr. 19, 1994

[54] CAPACITIVELY MEASURING CHEMICAL SENSOR SYSTEM

[75] Inventors: Bernd F. W. Hoffmann; Rainer Erbach, both of Karlsruhe; Gerhard Wegner, Mainz-Drais; Harald Fuchs, Carlsberg; Wolfgang Schrepp, Heidelberg; Matthias Schaub, Mainz, all of Fed. Rep. of Germany

[73] Assignee: BASF Aktiengesellschaft, Ludwigshafen, Fed. Rep. of Germany

[21] Appl. No.: 907,990

[22] Filed: Jul. 2, 1992

[30] Foreign Application Priority Data

Jul. 6, 1991 [DE] Fed. Rep. of Germany ........ 4122408

[51] Int. Cl.$^5$ .............................................. G01N 27/26
[52] U.S. Cl. ............................. 204/418; 204/416; 204/422; 204/433; 204/435
[58] Field of Search ............... 204/416, 418, 433, 435, 204/422

[56] References Cited
U.S. PATENT DOCUMENTS

| | | | |
|---|---|---|---|
| 4,269,682 | 5/1981 | Yano et al. | 204/435 |
| 4,508,613 | 4/1985 | Busta et al. | 204/418 |
| 5,011,589 | 4/1991 | Amemiya et al. | 204/416 |
| 5,182,005 | 1/1993 | Schwiegk et al. | 204/435 |

Primary Examiner—John Niebling
Assistant Examiner—Bruce F. Bell
Attorney, Agent, or Firm—Keil & Weinkauf

[57] ABSTRACT

In a miniaturizable, capacitively measuring chemical semiconductor-based sensor system consisting of a sensor and a reference element which are to be brought into contact with the electrolyte to be measured, the reference element being connected in series with the sensor, the reference element consists of a highly doped semiconductor substrate or metal/semiconductor substrate which is covered with a membrane, and the sensor consists of an insulator/semiconductor substrate which is coated with a sensitive membrane, and the sensitive membrane of the sensor is more sensitive than that of the reference element.

The sensor and the reference element of this sensor system may either be applied to one and the same chip or consist of individual components which are readily interchangeable with one another.

9 Claims, 10 Drawing Sheets flexible Seitenketten

α-Helix

CAPACITIVELY MEASURING CHEMICAL SENSOR SYSTEM

The present invention relates to a capacitively measuring chemical semiconductor-based sensor system for measuring concentrations in liquid electrolytes, part of the system consisting of the actual sensor and the other part of a reference element, which are connected in series with one another in a manner such that the use of conventional reference electrodes (Ag/AgCl or calomel electrodes) can be dispensed with. This permits miniaturization for compatibility with semiconductor technology. The conversion from a chemical to an electrical signal is effected with the use of the known field effect.

The design of integrated chemical sensors based on ion-selective field effect transistors is known and is, described by, for example, J. Janata and R. J. Huber in Solid State Chemical Sensors, Academic Press, New York, 1985, Chapter 2, page 66 and Chapter 3, and by A. Sibbald, Recent advances in field-effect chemical microsensors, J. Mol. Electron. 2 (1986), 51 to 83. The use of CHEMFETs as online sensors for monitoring chemical processes is prevented by certain still unsolved problems, in particular by a lack of long-term stability and poor adhesion of the chemically sensitive layer. A few years ago, Langmuir-Blodgett films (LB films) (cf. J. Am. Chem. soc. 57 (1935), 1007-1022) were proposed as alternatives to the conventionally applied polymers usually used, such as PVC or polyvinyl alcohol (cf. G. G. Roberts, An applied science perspective of Langmuir-Blodgett films, Adv. Phys. 34 (1985), 1-38). However, the usual LB films of amphiphilic substances have the same stability problems. With LB films of phthalocyaninato-polysiloxane polymers, a substance was recently found which proved to be very advantageous as the ion-sensitive part in electrolyte/isolator/semiconductor (EIS) structures with regard to long-term stability and sensitivity to protons and shows no cross-sensitivity to alkali metal ions (cf. A. Vogel, B. Hoffmann, Th. Sauer and G. Wegner: Langmuir-Blodgett Films of Phthalocyaninato-Polysiloxane Polymers as a novel Type of CHEMFET Membrane; Sensors and Actuators, Vol. B1 (1990), pages 408-412; Elsevier Sequoia/Printed in the Netherlands). DE-A 40 17 905 also proposed a reference electrode for chemical sensors based on ion-selective field effect transistors (CHEMFETs) which carry thin polyglutamate (=PG) layers as an insensitive membrane on insulator/semiconductor substrates.

It is an object of the present invention to provide a capacitively measuring chemical sensor system which comprises a sensor and a reference element and is simple to prepare, has very low cross-sensitivity and is suitable for miniaturization, its individual components being easily replaceable.

We have found, surprisingly, that this object is achieved if a sensitive membrane is applied to an insulator/semiconductor substrate and the insensitive membrane is applied to a highly doped semiconductor substrate or metal/semiconductor substrate, the latter having no field effect and acting only as a supporting electrode. Furthermore, precisely the converse structure is possible, i.e. the insensitive membrane on an insulator/semiconductor substrate and the sensitive membrane on a highly doped semiconductor substrate or metal/semiconductor substrate.

The present invention relates to a miniaturizable, capacitively measuring chemical semiconductor-based sensor system., consisting of a sensor and a reference element which are to be brought into contact with the measuring solution (electrolyte), wherein the reference element is connected in series with the sensor, the reference element consisting of a highly doped semiconductor substrate or metal/semiconductor substrate which is covered with a membrane and the sensor consisting of an insulator/semiconductor substrate which is coated with a sensitive membrane, and the sensitive membrane of the sensor being more sensitive than that of the reference element.

The difference between the sensitivity of the sensor membrane and that of the reference element membrane, expressed by the ratio of voltage difference to concentration change (measured in mV/negative logarithm of the concentration), is preferably twice as great as the sensitivity of the reference element.

In this sensor system, the sensitive sensor membrane may be applied to a highly doped semiconductor substrate or a metal/semiconductor substrate and the less sensitive membrane to an insulator/semiconductor substrate.

The sensor and reference element may either be applied to one and the same chip or may consist of individual components which can readily be interchanged with one another.

In the novel sensor system, the sensor membrane may preferably consist of the same base material as the membrane of the reference element, and the sensor membrane can be rendered sensitive by introducing or binding groups having a selective action.

The membranes for the novel sensor system may have been applied by the Langmuir-Blodgett method or by vapor deposition, sputtering, epitaxial growth, CVD (=chemical vapor deposition) or spincoating on the substrates.

Preferably used base membranes are organic polymers, for example poly($\gamma$-methyl L-glutamate-co-$\gamma$-n-alkyl L-glutamate), where n-alkyl is $C_{10}H_{21}$ to $C_{25}H_{51}$ and the n-alkyl L-glutamate content is from 20 to 40%.

For the production of an $Na^+$ sensor, the membranes for the reference element and the sensor may consist of polyglutamate, the sensor membrane having been rendered sensitive to $Na^+$ ions by the introduction of ionophores.

The sensitivity obtained in the novel system is the difference between the sensitivity of the sensor membrane and that of the reference membrane. According to the invention, the sensitivity is understood as meaning the shift in the capacitance/voltage curves (=C/V curves) as a function of the concentration in the electrolyte along the voltage axis.

The covering of the substrates with the membranes may be effected by any conventional method which permits the reproducible production of membrane thicknesses of from a few nm to a few $\mu$m, in particular by the Langmuir-Blodgett method, vapor deposition, sputtering, epitaxial growth, CVD or spincoating.

The Langmuir-Blodgett method, the apparatuses suitable for this purpose and the preconditions for the feasibility of this method are known, and are described in, for example, G. L. Gaines, Insoluble Monolayers at Liquid-Gas Interfaces, Interscience Publishers, 1966.

The particular advantages of the present invention are the simple production of the sensor system or of the individual components sensor and reference element compared with the expensive production of CHEMFETs, the possibility of miniaturization, the simple and inexpensive replacement of the sensor system or the individual components where the holder has a suitable architecture, the possibility of integrating different sensors and reference elements on a chip or of using them as individual components, for example in a flow-through cell, and the substantial compensation of cross-sensitivities, drifts and temperature and light effects.

This is achieved in particular if the sensor membrane and the reference membrane consist of the same base material, and the sensor membrane can be rendered selective by introducing or binding sensitive groups specifically for the desired application.

A further advantage is that the reference element is connected simply in series with the sensor, and the conventional reference electrode can thus be replaced without changes to the circuit.

BRIEF DESCRIPTION OF THE DRAWINGS

Regarding the composition of the novel sensor system the following may be stated specifically:

FIG. 2(A): In this Figure, the numbers 1–6 have the same meanings as in FIG. 1, 8=insensitive membrane e.g. polyglutamate=PG), 9=tap on upper surface of the substrate.

FIG. 2(B): In this Figure, the numbers 1–8 have the same meanings as in FIG. 2(A), 10=metal or highly doped semiconductor substrate (e.g. $n^+$-Si).

FIG. 2(C): The numbers 1–3 and 6 have the same meanings as in FIG. 1, 10=highly doped semiconductor substrate (e.g. $n^+$-Si), 8=insensitive membrane (e.g. PG).

FIG. 2(D): The numbers 1–10 have the same meanings as in FIG. 2(C).

Further preferred poly($\gamma$-methyl L-glutamate-co-$\gamma$-n-alkyl L-glutamates) are those in which n-alkyl is $C_{10}H_{21}$ to $C_{25}H_{51}$ and the n-alkyl L-glutamate content is from 20 to 40 mol %. These copolyglutamates which are used may have any degree of polymerization, but preferably a degree of polymerization of from 20 to 2,000, a helical structure being preferred. These copolymers can be particularly advantageously applied by the Langmuir-Blodgett method to the substrates to be coated. For this purpose, they are generally dissolved in a suitable organic solvent, preferably in a halohydrocarbon, e.g. chloroform, the concentration of the PG in the solvent advantageously being from 0.001 to 0.1%, for example about 0.02%. Coating is effected with the aid of a Lauda film balance over which a highly clean-room atmosphere is produced by means of a laminar flow box. The copolyglutamate solution is spread over a thermostated subphase comprising very pure water and is compressed to a surface tension of 20 mN/m after the solvent has been evaporated off, and, after a constant film surface area has been achieved, the substrate to be coated is advantageously immersed through the polymer film into the subphase by a Lauda film lift at a rate of 10 mm/min. In this way, a monolayer is transferred during each immersion and withdrawal. After transfer of the desired number of monolayers, which may be from 2 to 60, the substrate is dried and if necessary heated.

Where homopolyglutamates, e.g. poly($\gamma$-methyl L-glutamate) or poly($\gamma$-benzyl L-glutamate), which are likewise suitable, may be used for coating the insulator/semiconductor or highly doped semiconductor substrates or metal/semiconductor substrates, this is advantageously effected by spincoating (at from 500 to 2,000 rpm), and subsequent removal of the solvent or by vapor deposition or sputtering. Correspondingly thin and effective layers can also be produced in this manner.

The preparation of suitable polyglutamates and copolyglutamates is described in, for example, EP-A 03 00 420. Instead of the polyglutamates, it is also possible to use other organic polymers, for example cellulose derivatives, as membrane material.

The layer thickness of the membranes for the sensor or the reference element may be from a few nm to a few $\mu$m, for example from 2 nm to about 5 $\mu$m. In addition to the LB method, spincoating, vapor deposition, epitaxial growth, CVD and sputtering are also suitable for coating, as described in, for example, I. Ruge, Halbleitertechnologie, Springer-Verlag (1984), (pages 67, 82, 134, 263 and 265).

The novel sensor system is particularly advantageous if, for the sensor and the reference element, the membranes consist of the safe base material, for example the abovementioned PG, and the sensor membrane may be rendered selective in a specific manner by mixing in ionophores.

Figure 5:
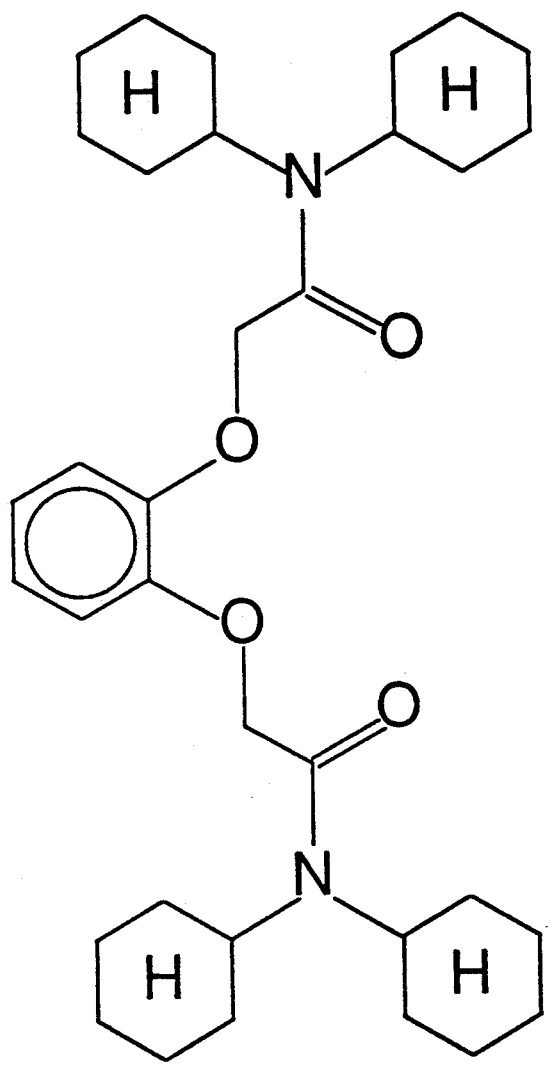
FIG. 5 shows the formula of a commercial Na ionophore, which can be mixed with the PG in a ratio of 1–10%, based on the number of monomers in the PG.

FIG. 5 shows the formula of a commercial Na ionophore, which can be mixed with the PG in a ratio of 1–10%, based on the number of monomers in the PG, with the result that the sensor membrane can detect $Na^+$ ions.

Suitable semiconductor/insulator substrates for the novel sensor system are silicon/$SiO_2$, Si/$SiO_2$/$Si_xN_y$ (in which preferably x=3 and y=4), Si/SiO$_2$/ZrO$_2$, germanium/GeO$_2$ and III-V semiconductors, such as GaAs and GaInP with insulating layers instead of an oxide. A preferred semiconductor/insulator substrate is Si/SiO$_2$, in particular p-Si/SiO$_2$, for example p-doped silicon wafers having a conductivity of 17-30 1/$\Omega$cm and a SiO$_2$ layer thickness of 50±5 nm.

Suitable highly doped semiconductors for the novel sensor system are silicon, germanium and III-V semiconductors, such as GaAs or GaInP, which may be doped until degenerate, for example by ion implantation or diffusion, so that they exhibit quasi-metallic behavior. Highly doped p- or n-silicon substrates having a degree of doping greater than 10$^{18}$ 1/cm$^3$ and a conductivity of more than 0.1 1/$\Omega$cm are preferred. Suitable metals for the metal/semiconductor substrates are all metals which have a conductivity of more than 0.1 1/$\Omega$cm, in particular gold and aluminum on p-Si or chromium and nickel on n-Si. Pure metallic substrates, in particular of the stated metals, are in principle also possible.

The sensor system may be composed either individually of the sensor and the reference element, depending on the desired use, or both parts are integrated on a chip completely compatible with semiconductor technology.

Figure 1:
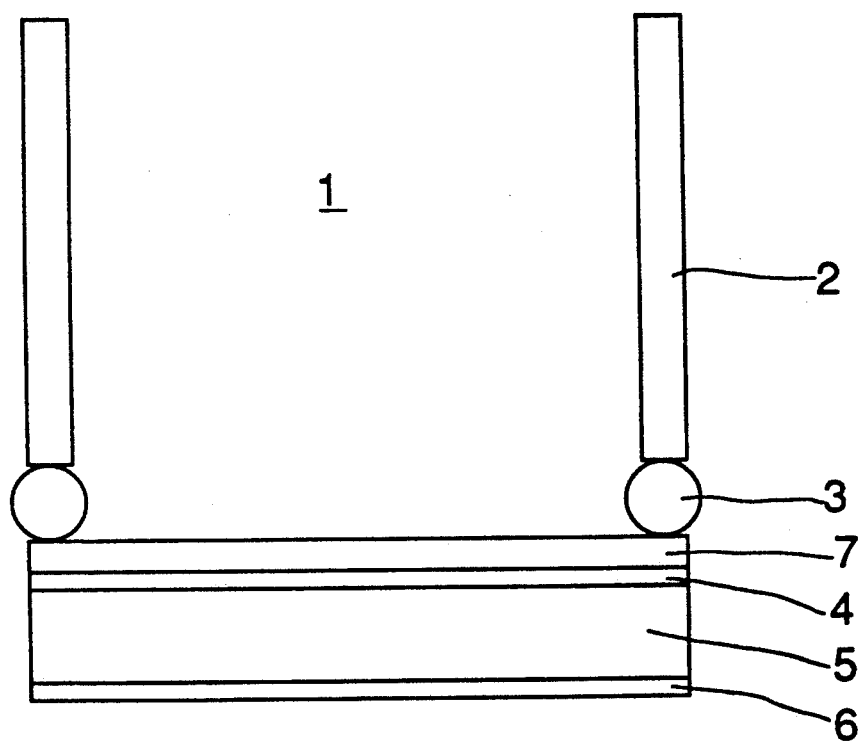
FIG. 1 schematically shows in principle the composition of a capacitive sensor as usually used in electrolyte/insulator/semiconductor systems. In the Figure, 1=electrolyte, 2=electrolyte vessel, 3=seal, 4=insulator (e.g. $SiO_2$), 5=semiconductor (e.g. p-Si), 6=metallization (e.g. gold or aluminum), and 7=sensitive membrane (e.g. $Si_3N_4$).
Figure 2A:
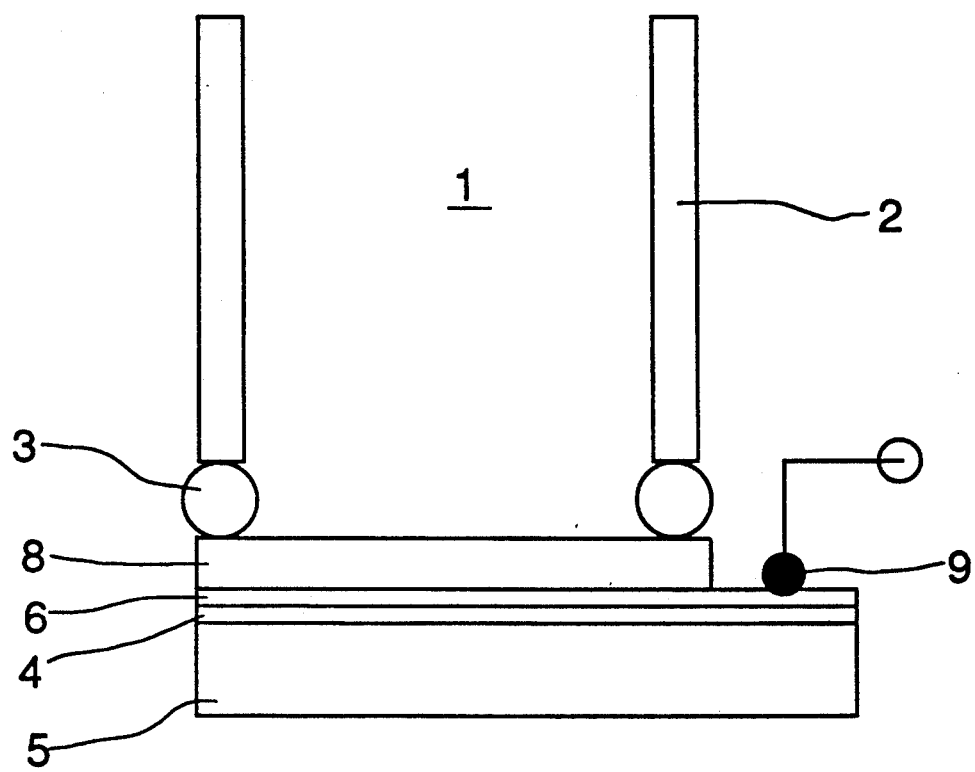
FIGS. 2a–d show in principle the possible compositions of the reference element.
Figure 2B:
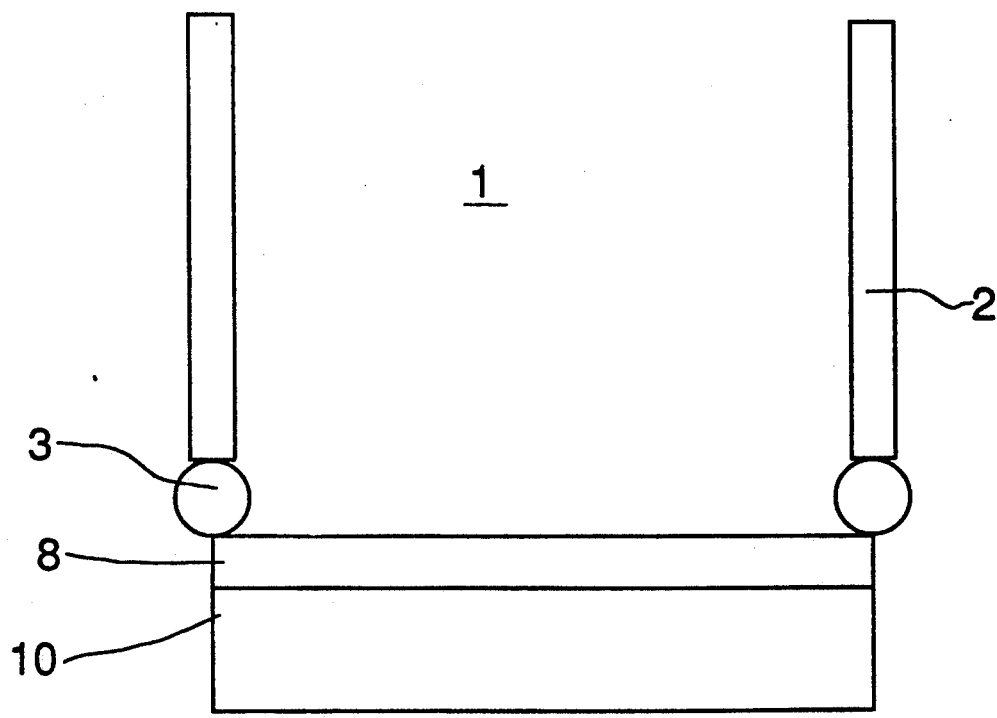
Figure 2C:
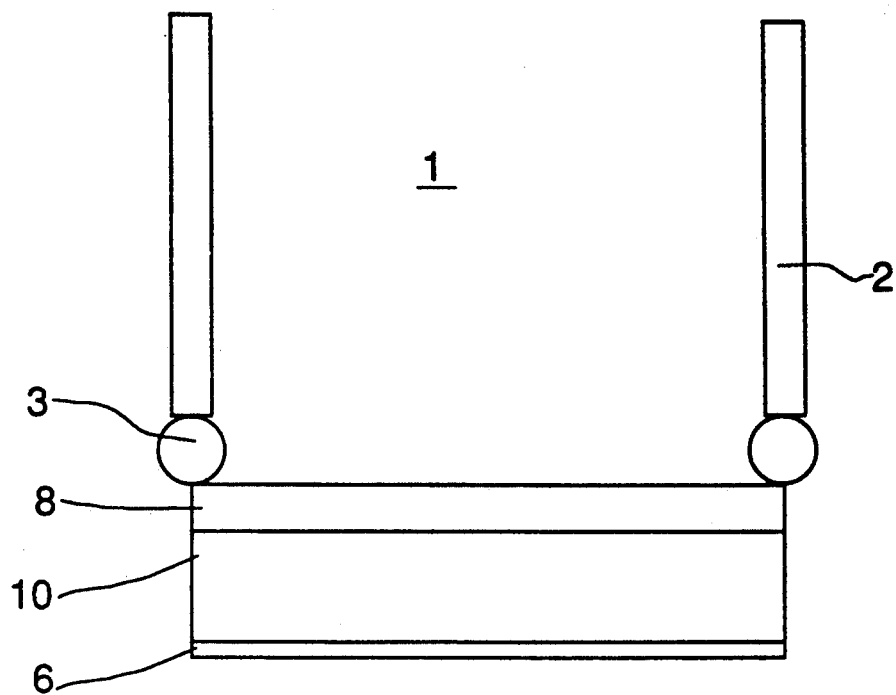
Figure 2D:
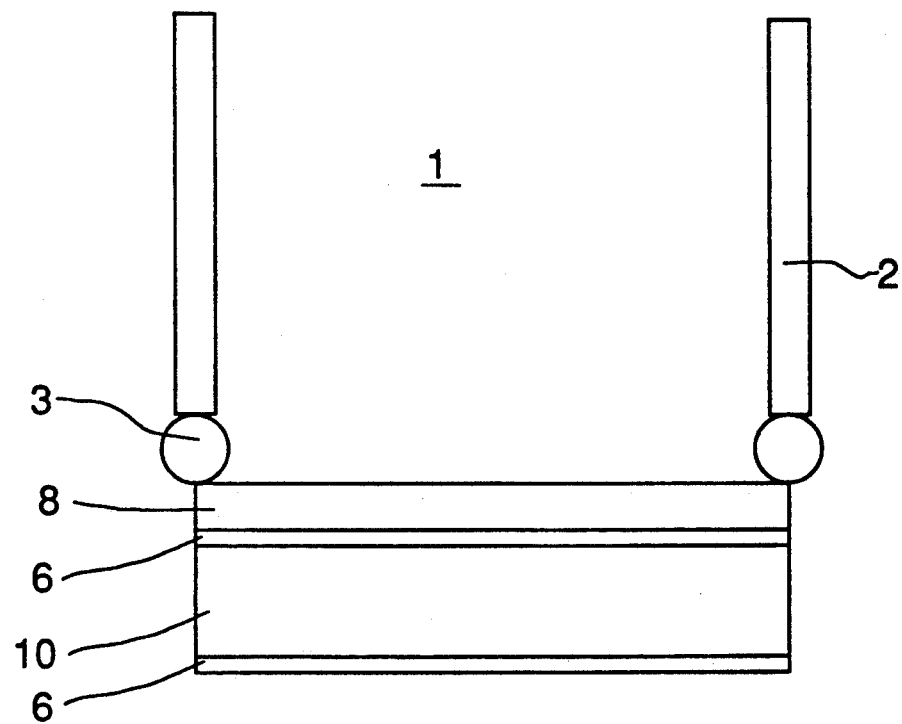
Figure 3:
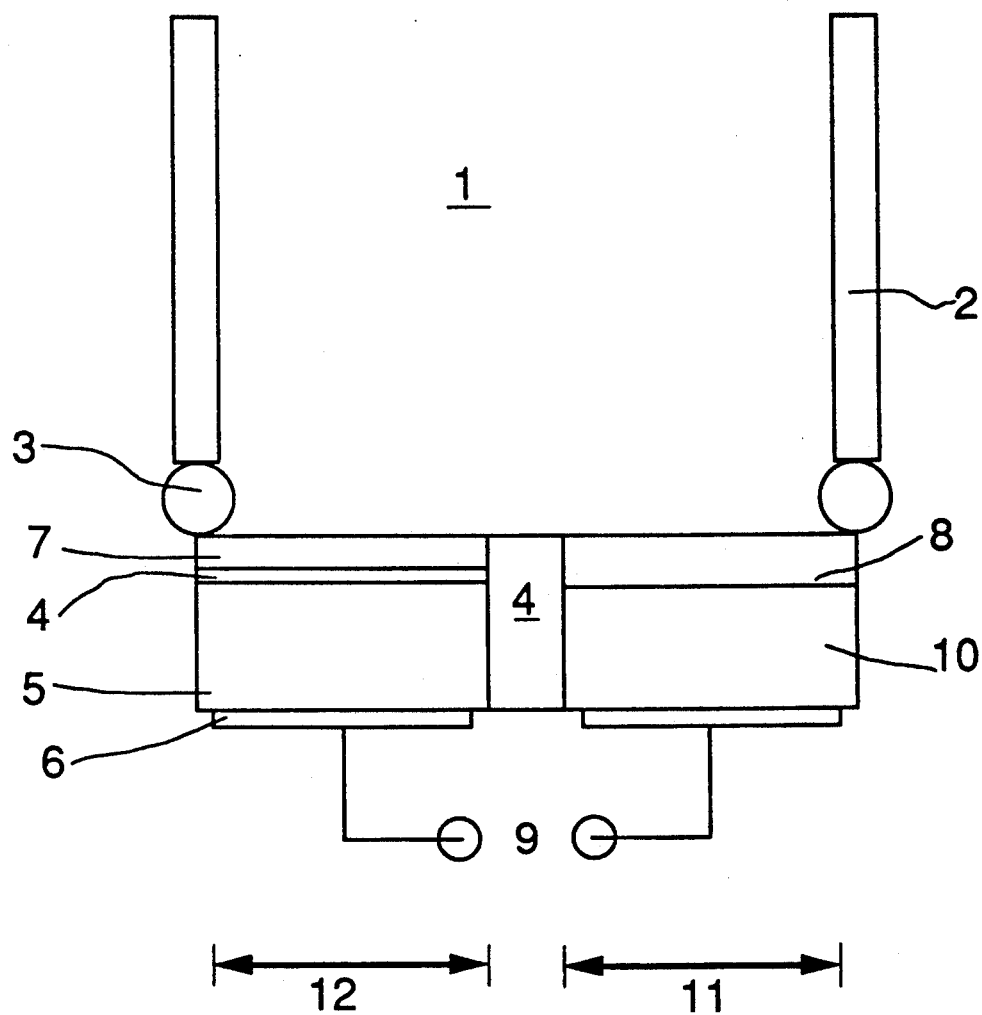
FIG. 3 shows the complete capacitive sensor system, where 12=sensor and 11=reference element either on one chip, separated by an insulator=4 or may also be spatially separated. The numbers 1–6 have the same meanings as in FIG. 1, 8=insensitive membrane (e.g. PG), 7=sensitive membrane (e.g. $Si_3N_4$), 9=electrical connection, 10=highly doped semiconductor substrate (e.g. $n^+$-Si). Sensitive and insensitive membranes may also be interchanged with one another.
Figure 4:
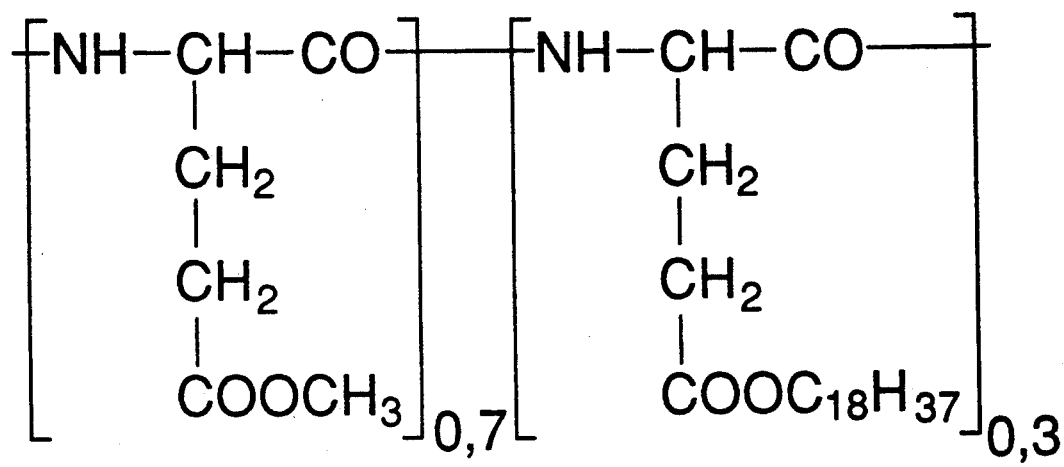
FIG. 4 shows the formula of poly($\gamma$-methyl L-glutamate-co-$\gamma$-n-alkyl L-glutamate) as an example of a preferred membrane material, 70 mol % of $\gamma$-methyl L-glutamate units and 30 mol % of $\gamma$-n-octadecyl L-glutamate units being present.
Figure 4:
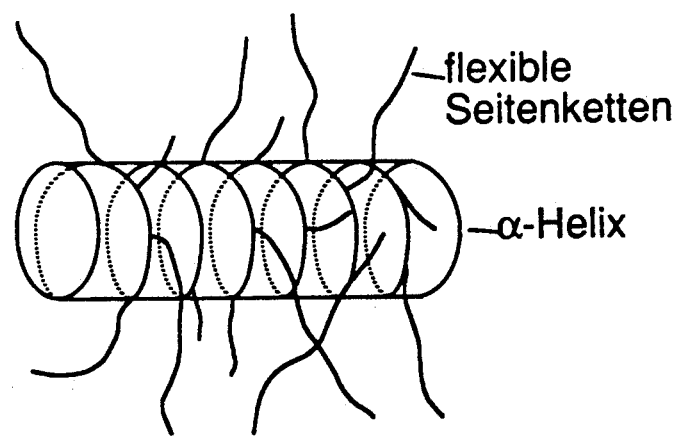

The Examples which follow are constructed as sensor systems according to FIG. 3, the sensor and reference element being present on separate substrates and being positioned so that both have contact with the electrolyte solution.

In the Examples which follow, parts and percentages are by weight, unless stated otherwise.

EXAMPLE 1

The sensor used was an Al/Si/SiO$_2$/Si$_3$N$_4$ wafer (obtained from the Fraunhofer Institute, Munich).

Wafers of highly doped (doping density 10$^{19}$ 1/cm$^3$) n-silicon were used for the reference element. Before coating, they were treated with 10% strength HF for 15 minutes in order to remove oxide layers completely. To render them water-repellant, the wafers may additionally be silanized with a 40% strength solution of hexamethyl-disilazane in chloroform at 40° C.

The Langmuir-Blodgett (=LB) coating was effected on a Lauda film balance which was housed in a laminar flow box. Coating with PG was carried out as described above, a plurality of samples having different thicknesses (2-32 monolayers) being prepared. A contact of Al/Au was applied to the back of this reference element.

Both the pH sensor and the reference element measured 15×15 mm$^2$. They were installed in a special sample holder (flow-through cell) so that they were in contact with one another via the electrolyte solution. In addition, the pH sensor system could also be used for measurement against a conventional Ag/AgCl reference electrode (from Ingold). The entire system was housed in a lightproof metal box. The C/V curves were recorded using a Hewlett-Packard 4272 LCR meter and a connected PC. The bias voltage was altered in 100 mV steps in the range from −2,500 to +500 mV. The measuring frequency used was 1 kHz and the measuring a.c. voltage was 20 mV. The pH in the measuring cell was changed under computer control by titration of a 0.1 m KCl solution with NaOH and HCl.

Figure 6:
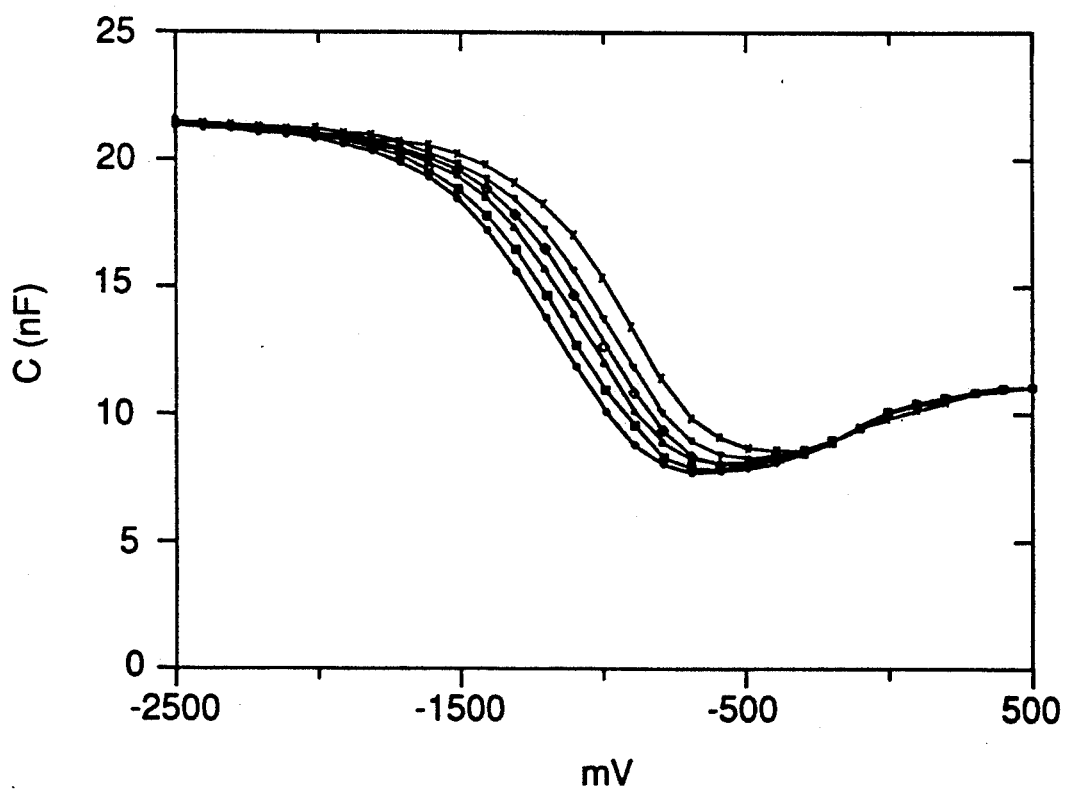
FIG. 6 shows the typical C/V curves as a function of the pH of the sensor system.
Figure 7:
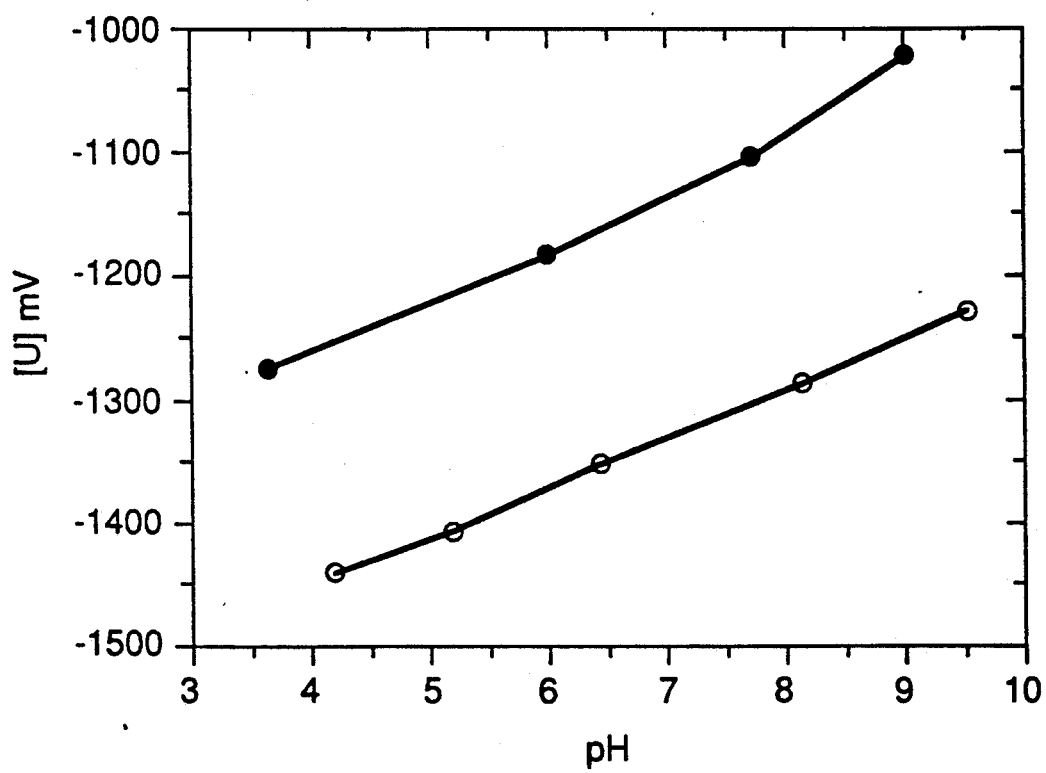
FIG. 7 shows a comparison of the evaluated C/V curves of the novel pH sensor system and a conventional measurement.

FIG. 6 shows the typical C/V curves as a function of the pH of the sensor system described above and consisting of a pH sensor and a reference element, and FIG. 7 shows a comparison of the evaluated C/V curves of the novel pH sensor system (lower curve) and a conventional measurement (pH sensor against Ag/AgCl reference electrode, upper curve). The excellent linearity of the novel sensor system is evident.

EXAMPLE 2

Na Sensor System

The reference element was produced as described in Example 1.

p-Doped Si wafers having a conductivity of 17-30 1/$\Omega$cm and an SiO$_2$ layer thickness of 50 nm were used for the production of a Na sensor. The sample size was 15×15 mm$^2$. For purification, the wafers were treated in succession with the following solutions, in each case at 40° C. in an ultrasonic bath: first, they were treated with acetone to remove the photoresist (10 minutes), after which they were rinsed with very pure water, then treated with a mixture of H$_2$SO$_4$, H$_2$O$_2$ and H$_2$O in a ratio of 1 : 1 : 5 (10 minutes), then rinsed with very pure water, and treated with a mixture of 25% strength NH$_3$, 30% strength H$_2$O$_2$ and H$_2$O in a ratio of 1 : 1 : 5 (60 minutes), rinsed with very pure water, treated with 10% strength HCl (2 minutes), rinsed with very pure water and then dried in a drying oven at 50° C.

The chemicals used were analytical grade and the very pure water was obtained with a plant for very pure water (Seral pro 90).

Water repellency was imparted as described in Example 1.

The membrane material used was the abovementioned PG, and the Na ionophore III (Fluka) was additionally mixed in, so that there was exactly 1 ionophore per 9 repeating units of the PG.

The material was applied by the LB method as described above. To prevent the ionophores from diffusing out, a further pure PG layer (2 monolayers) was additionally applied over the sensor membrane.

The Na sensor was installed together with the reference element in the abovementioned sample holder.

The measurement was carried out as described above, except that in this case solutions having different Na concentrations were introduced by hand (Na concentration from 10$^{-6}$ to 10$^{-1}$ molar, corresponding to pNa=1 to 6; NaCl in TRIS buffer (=tris(hydroxymethyl)-aminomethane)).

Figure 8:
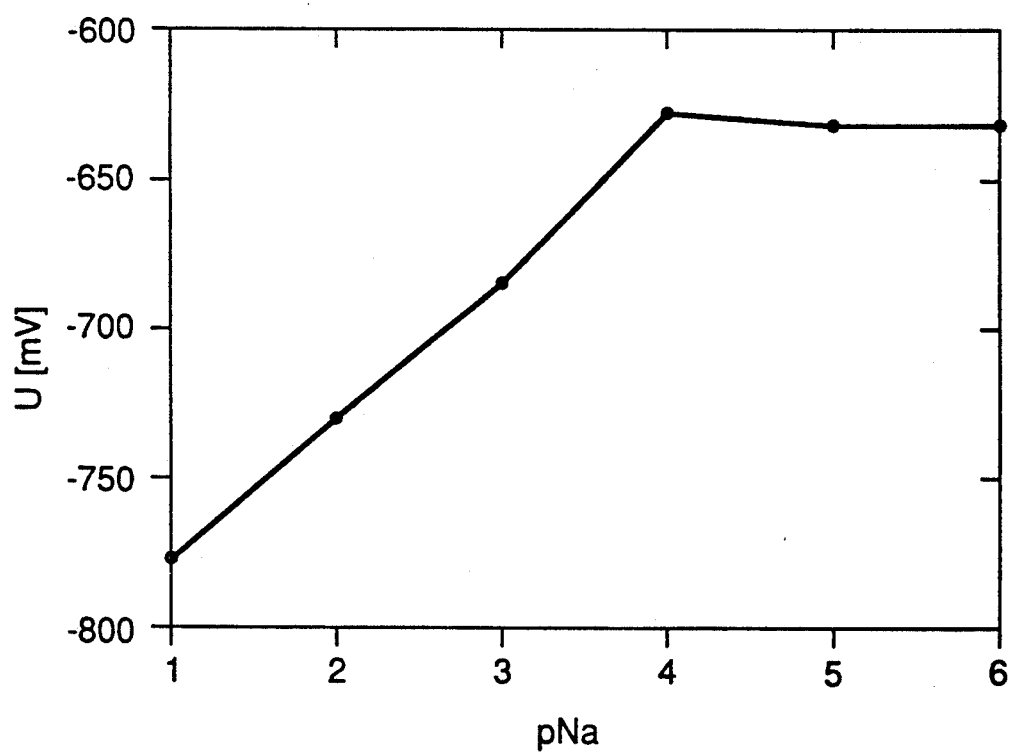
FIG. 8 shows the evaluated curves as a function of the Na concentration.

The evaluated C/V curves, i.e. the voltage shift of the curves as a function of the Na concentration, are shown in FIG. 8. The high Na$^{61}$ sensitivity in the range from pNa=1 to pNa=4 (over 50 mV/pNa) is evident.

Figure 9:
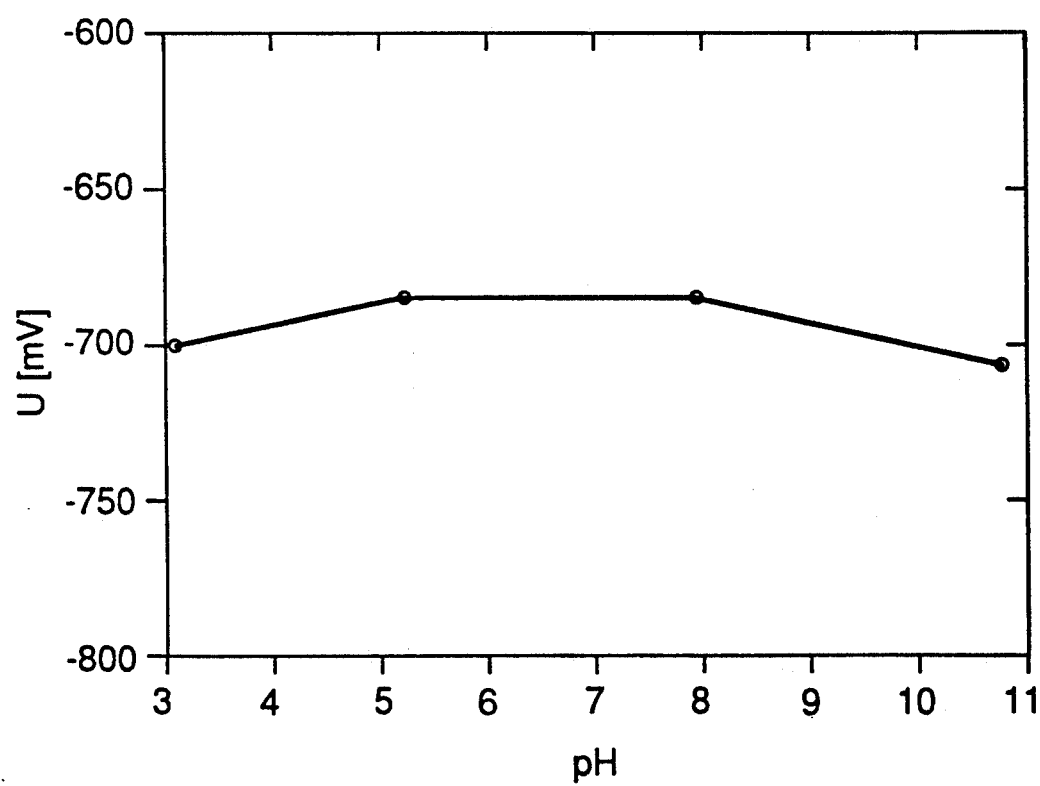
FIG. 9 shows the results of the automated compensation of cross sensitivities, when the pH is changed from 3 to 11 with the automated titration at a fixed Na concentration of 0.1M NaCl.

To demonstrate the automatic compensation of cross-sensitivities, the pH was changed from 3 to 11 with automatic titration at a fixed Na concentration of 0.1M NaCl. FIG. 9 shows the results. It can be seen that the starting signal remains virtually constant over 8 pH steps and there is therefore no cross-sensitivity to H$^{\oplus}$.

We claim:

1. A miniaturizable, capacitively measuring chemical semiconductor-based sensor system, consisting of a sensor and a reference element which are to be brought into contact with an electrolyte solution, wherein the reference element is connected in series with the sensor, the reference element consisting of a highly doped semiconductor substrate or metal/semiconductor substrate which is covered with a membrane, and the sensor consisting of an insulator/semiconductor substrate which is coated with a sensitive membrane, and the sensitive membrane of the sensor being more sensitive than that of the reference element.

2. A sensor system as claimed in claim 1, wherein the difference between the sensitivity of the sensor membrane and that of the reference element membrane, expressed by the ratio of voltage difference to concentration change (measured in mV/negative logarithm of the concentration) is twice as great as the sensitivity of the reference element.

3. A sensor system as claimed in claim 1, wherein the sensor and the reference element consist of individual components which can readily be interchanged with one another.

4. A sensor system as claimed in claim 1, wherein the membranes have been applied to the substrates by the Langmuir-Blodgett method.

5. A sensor system as claimed in claim 1, wherein the membranes have been applied to the substrates by vapor deposition, sputtering, epitaxial growth, CVD or spin coating.

6. A sensor system as claimed in claim 1, wherein an organic polymer is used as the base membrane.

7. A sensor system as claimed in claim 1, wherein a poly($\gamma$-methyl L-glutamate-co-$\gamma$-n-alkyl L-glutamate), in which n-alkyl is $C_{10}H_{21}$ to $C_{25}H_{51}$ and the n-alkyl L-glutamate content is from 20 to 40%, is used as the base membrane.

8. A sensor system as claimed in claim 7, wherein the sensor membrane has been rendered sensitive to $Na^+$ ions by the introduction of ionophores.

9. A sensor system as claimed in claim 1, wherein the sensor membrane and the reference element membrane consist of the same base material prior to rendering sensitive the sensor membrane by introduction or binding of groups having a selective action.

* * * * *